United States Patent [19]

Stolk et al.

[11] Patent Number: 4,797,313

[45] Date of Patent: Jan. 10, 1989

[54] NON-METALLIC POLYMERIC TWIST TIE

[75] Inventors: Richard D. Stolk, Manchester; Vladimir O. Bekker, Olivette, both of Mo.

[73] Assignee: Monsanto Company, St. Louis, Mo.

[21] Appl. No.: 796,662

[22] Filed: Nov. 8, 1985

[51] Int. Cl.$^4$ ............................................. B32B 3/02
[52] U.S. Cl. .................................... 428/156; 428/99; 428/480; 24/30.5 P; 24/30.5 T
[58] Field of Search ............ 428/156, 189, 424.2, 428/424.7, 99, 480, 518; 24/30.5 R, 30.5 T, 30.5 P, 30.5 S, 16 PB; 132/44, 43 R

[56] References Cited

U.S. PATENT DOCUMENTS

| | | | |
|---|---|---|---|
| 3,535,746 | 10/1970 | Thomas, Jr. ................. | 24/30.5 T |
| 3,565,738 | 2/1971 | Kirkpatrick .................. | 161/38 |
| 3,604,066 | 9/1971 | Moon ............................ | 24/30.5 R |
| 3,896,991 | 7/1975 | Kozlowski et al. ........... | 428/189 |
| 3,945,086 | 3/1976 | Hoard ........................... | 24/30.5 T |
| 3,974,960 | 8/1976 | Mitchell ....................... | 24/30.5 P |
| 4,096,202 | 1/1978 | Farnham et al. . | |
| 4,358,446 | 11/1982 | Stevenson .................... | 426/106 |
| 4,444,949 | 4/1984 | Liu . | |
| 4,510,287 | 4/1985 | Wu ................................ | 525/84 |

*Primary Examiner*—George F. Lesmes
*Assistant Examiner*—Betsy Bozzelli
*Attorney, Agent, or Firm*—Thomas E. Kelley; William J. Farrington

[57] ABSTRACT

Essentially organic, non-metallic ribbon useful as a twist tie comprising polymeric material exhibiting glass/rubber transitional behavior. Polymeric ribbons deformed under tensile stress at 25° exhibit yield stress between about 500 and 9,000 psi. Discrete lengths of ribbon are capable of being disengagedly formed into fastly held twist ties by rotationally deforming terminal ends of said lengths about each other. Ribbons can comprise polymers, such as polyalkylene terephthalates, polyvinylchlorides, styrene-acrylonitrile copolymers and polystyrenes. Optional polymeric materials include elastomeric impact modifiers and plasticizers. Process for the production of such ribbon. Methods for using such ribbon.

18 Claims, 1 Drawing Sheet

NON-METALLIC POLYMERIC TWIST TIE

BACKGROUND OF THE INVENTION

The invention of this application relates to non-metallic polymeric twist ties.

Throughout the specification, percentages of compositions are by weight and temperatures are in degrees Celsius unless indicated otherwise.

Twist ties comprising a middle wire centrally enclosed in a plastic or paper ribbon are ubiquitously used as closures, for instance to seal plastic bags, to fasten plants to stakes, to secure bundled electric cable, and for other fastening requirements. The widespread use of such ties results from the numerous advantageous properties. For instance, the same twist tie which can be applied mechanically, e.g. to bread bags and the like, in a high speed operation can also be applied manually in a somewhat slower speed operation with little physical exertion other than rotational twisting with the finger tips. Such metal twist ties can be multiply refastened with little reduction in fastening capability, for instance such ties can be reused up to ten times or more without failure. Moreover, such ties can be twisted without regard to directional rotation. In fact, such ties can be alternatively twisted in opposing rotational directions. Metal twist ties are also functional, i.e. can be tied, untied, retied and will hold with a secure twist, over a wide range of temperatures, e.g. from less than minus 10° to greater than 65°.

Such metal twist ties are not universally used, however, for many food packaging applications because of certain disadvantageous properties. For instance, many convenience foods are packaged so that they can be heated in their original packaging in microwave ovens. Metal twist ties however will cause undesirable arcing when subjected to microwave radiation at an intensity common to such ovens.

In other cases it is common practice to inspect packaged food, e.g. sliced bread, for the possible presence of alien metal, e.g. chips, grit or filings from cutting blades or other mechanical equipment. In this regard it is desirable to inspect such sliced food products with metal detectors after final packaging. The use of metal twist ties hinder such practice. Accordingly, many sliced food products and microwavable convenience foods are packaged in plastic bags fastened by non-metallic closures, such as flat strip polymeric closures having bag neck confining apertures, such as disclosed in U.S. Pat. No. 3,164,250, or adhesive tapes. Flat strip polymeric closures are often undesirable because of their relatively high cost and inferior sealing capability. Adhesive tapes are undesirable because they are difficult to unfasten and generally have no refasten capability.

There have been a number of attempts to produce non-metallic polymeric twist ties with the desirable properties of metal twist ties. Such attempts have heretofore failed to replicate a sufficient number of the desirable properties of metal twist ties to provide a generally acceptable tie. For instance, polymeric ties have been prepared from plasticized polyvinylchloride ribbon containing up to about 20% or more of plasticizer. The effect of such high levels of plasticizer is to reduce the glass transition temperature of the polymer, e.g. to less than about 30°. When such highly plasticized ties are exposed to temperatures near or above the glass transition temperature, twisted ties readily untwist. Such ties are effective only when tied into a knot.

Alternatively it has been proposed that polymeric twist ties be prepared from unplasticized polyvinylchloride. In this regard see Kirkpatrick who discloses in U.S. Pat. No. 3,565,738 polymeric ties in the form of a semi-rigid tape made of plastic material having a high tensile modulus and dead fold characteristics similar to those of a wire. Polymers disclosed by Kirkpatrick have been found to be unadaptable to mechanical twist tie apparatus.

Other non-metallic polymeric closures, e.g. for plastic bags, are disclosed in U.S. Pat. Nos. 3,334,805; 3,535,746; 3,604,066; 3,662,434; 3,945,086; 3,974,960 and 4,079,484.

OBJECTS OF THE INVENTION

An object of this invention is to provide a non-metallic polymeric twist tie which is useful for sealing bags by hand as well as by mechanical twist tie apparatus.

Another object is to provide polymeric non-metallic twist ties that are functional, i.e. can be tied, untied, retied and will hold fast, over a wide temperature range of expected use.

Another object is to provide a non-metallic polymeric twist tie that can be subjected to microwave radiation ovens.

Another object is to provide a polymeric non-metallic twist tie that can be manually untied and retied throughout the common service life of twist ties.

Another object is to provide a non-metallic polymeric twist tie that can functionally replace metal twist ties in existing automatic tying equipment. In some embodiments it is an object that such polymeric non-metallic twist ties will remain fastly twisted when subjected to high, but not uncommon, ambient temperatures. In many cases this is difficult to achieve together with the requirement that such twist ties be equally functional at lower ambient temperatures.

Other objects of the invention include specific polymeric compositions that advantageously are extrudable into polymeric twist ties having a wide number of common properties with metal twist ties.

These and other objects of the invention will be more readily apparent from the following detailed description.

SUMMARY OF THE INVENTION

It has been discovered that the foregoing objectives can be realized with an essentially organic, non-metallic ribbon comprising a polymeric material having a glass transition temperature greater than about 30° and which exhibits glass/rubber transitional behavior in a temperature range from about 10° to about 40°. When such polymeric ribbon is deformed under tensile stress at 25°, it will exhibit yield at a stress between about 500 and about 9,000 pounds per square inch (psi). Discrete lengths of such ribbon are thereby capable of being disengagedly formed into fastly held twist ties by rotationally deforming terminal ends of said lengths about each other.

In many embodiments, such objectives can be more advantageously realized by providing a ribbon which, when deformed under tensile stress at a strain rate between 0.1 and 0.5 inches per inch per minute (ipipm), will exhibit strain softening, often characterized as necking. In many preferred embodiments, such objectives are advantageously realized by providing a ribbon which will deform under tensile stress at least 10% in elongation after yield.

In preferred embodiments of the invention such objectives can be advantageously realized by providing a ribbon comprising at least about 50% by weight of one or more thermoplastic polymers selected from the group consisting of polyalkylene terephthalate, styrene acrylonitrile copolymer, polystyrene and polyvinylchloride and, in many preferred embodiments, up to about 50% by weight of a particulate elastomeric impact modifier. It is generally desirable that such ribbons have a cross-sectional area that is substantially uniform over its length, and in many cases that such ribbon have at least one rib along its length.

This invention also provides processes for producing such ribbons and methods for employing such ribbons, for instance for closing and securing a bag using such ribbon as a twist tie.

DETAILED DESCRIPTION OF THE INVENTION

As used in the specification and the appended claims the term "ribbon" denotes a filamentary segment which has a length which is very large as compared to its cross-sectional dimensions. Such ribbon may be substantially thin and flat, or have an irregular cross-section, such as a thin flat section with one or more ribs. Such ribbon can be provided in virtually any length desired for the use intended.

The term "essentially organic" is used to denote material used in the ribbon of this invention that comprises organic polymers, i.e. thermoplastic or elastomeric polymers. Such essentially organic materials may exist as a single phase, e.g. a mixture or blend of compatible organic polymers, or in multiphases, e.g. as a mixture of non-compatible organic polymers.

The term "non-metallic" denotes a material that is devoid of a reduced metal phase, e.g. a continuous reduced metal phase such as a metal wire. The essentially polymeric material used in the ribbon of this invention may however comprise dispersed metal salt or metal oxide, such as extenders, stabilizers, lubricants, processing aids and the like.

The term "glass transition temperature" means the temperature where the polymeric material of the ribbon of this invention undergoes a transition from the glassy state to the rubbery state. Glass transition temperatures are commonly determined by differential scanning calorimetry. Ribbons of this invention will comprise polymeric materials having glass transition temperatures of at least about 30°, or higher. In preferred embodiments, the polymeric materials will have glass transition temperatures of at least about 40°, or even 50°, and more preferably at least about 60° or 65°.

A glass/rubber transitional state represents a temperature range over which the polymeric material of the ribbon of this invention exhibits fracture behavior in tension which can be illustrated by reference to FIGS. 1, 2 and 3 of the drawings. In these drawings the ordinates, designated as "load" represent the application of tensile stress which is generally designated in units of pounds per square inch (psi) or mega pascals (MPa). The abscissas, denoted as "deformation", represents strain on the polymeric sample which is generally designated as percent elongation, i.e. change in length per unit of original length. Load/deformation curves and associated parameters such as tensile strength, yield stress and strain are readily determined in accordance with the American Society of Testing and Materials (ASTM) Standard Test Method D-882, entitled "Standard Methods of Test for Tensile Properties of Thin Plastic Sheeting", incorporated herein by reference.

Figure 1:
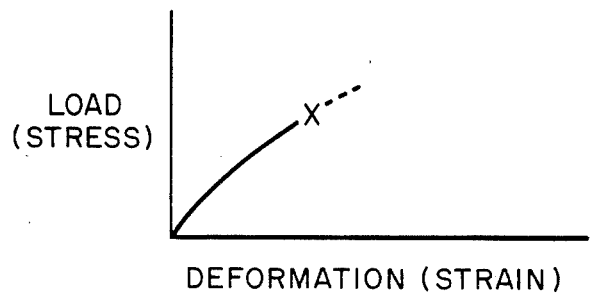
FIGS. 1, 2 and 3 illustrate load/deformation curves useful in characterizing the ribbon of this invention.

FIG. 1 illustrates a load/deformation curve for a a brittle polymeric material under tensile deformation. The "X" at the end of the curve indicates sample failure, i.e. catastrophic failure of the stressed sample by fracture. Such fracture can result when the intimate molecular forces are overcome in the weakest domains of the bulk of the material.

Figure 2:
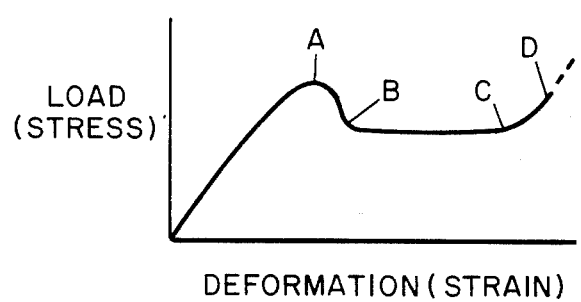

FIG. 2 illustrates a load/deformation curve for a polymeric material in a glass/rubber transitional state. Catastrophic failure of the stressed material, i.e. by fracture, may occur after deformation beyond the yield point (denoted by "A"), after deformation in a strain softening, i.e. necking, region (denoted by the region between points "A" and "B"), after deformation in an elongation region (denoted by the region between points "B" and "C") or during deformation in a strain hardening region (denoted by the region between points "C" and "D". While not intending to state a limitation of this invention, it is believed that a polymeric material, that exhibits elongation as indicated by a substantially horizontal curve in the B-C region, undergoes constant volume deformation without generation of voids. It is further believed that a polymeric material, that exhibits strain hardening as indicated by an upwardly-sloped curve as in the C-D region, undergoes deformation with a volume increase, e.g. by generation of voids, a phenomena generally referred to as "crazing". In some cases both types of deformation may occur simultaneously to various degrees, as indicated by a slightly upwardly-sloped curve in the B-C region.

Figure 3:
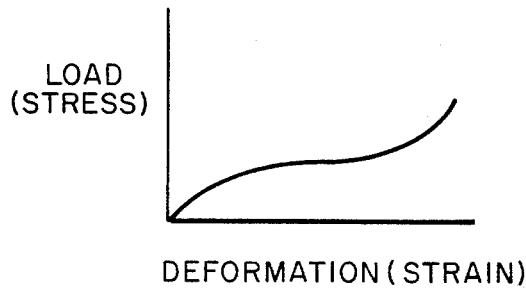

FIG. 3 illustrates a load/deformation curve for a resilient or rubber-like polymeric material under tensile deformation. Polymeric materials above the glass transition temperature will generally exhibit such rubber-like behavior.

Polymeric materials above its glass transition temperature, e.g. elastomeric materials or highly plasticized thermoplastic materials, will generally exhibit a load/deformation curve as illustrated in FIG. 3 regardless of the strain rate. It has also been discovered that polymeric materials that exhibit such resilient behavior at temperatures below about 30°, or in the case of preferred embodiments below higher temperatures, e.g. 40° or higher, say about 50°, are unacceptable for fabricating into ribbons of this invention. In more preferred embodiments polymeric materials exhibiting such resilient behavior at below even higher temperatures, say about 60° or 65°, are unacceptable for fabricating into ribbon. Such ribbons comprising resilient material will not maintain a fastly held twist tie at expected high exposure temperatures for the ribbon. However, other thermoplastic materials, e.g. non-elastomeric polymeric materials below the glass transition temperature may exhibit load/deformation curves as illustrated in FIG. 1 or 2 depending on the strain rate applied to the polymeric material.

It has been discovered that the selection of polymeric materials useful as twist ties according to this invention will have tensile properties characterized at strain rates that will approximate a strain rate experienced by the ribbon in automatic twist tie apparatus as well as strain rates experienced by the ribbon in manual twisting. Exemplary automatic twist tie apparatus is illustrated in U.S. Pat. Nos. 3,138,904 and 3,919,829, incorporated herein by reference. Polymeric materials formed into ribbons according to this invention may exhibit brittle-type behavior illustrated in FIG. 1 when subjected to stress at a high strain rate, e.g. at 10 ipipm, but yet exhibit glass/rubber transitional behavior as illustrated in FIG. 2 when subjected to stress at lower strain rates, e.g. 0.1 to 0.5 ipipm. In this regard it has been discovered that polymeric materials can be selected for fabricating ribbons that will function as twist ties according to this invention on the basis of exhibited glass/rubber transitional behavior between about 10° and 30°, e.g. at 25°, when subjected to tensile stress at strain rates between about 0.1 ipipm and between about 0.5 ipipm. Preferred materials will exhibit such glass/rubber transitional behavior between lower temperatures, say about 0°, or more preferably minus 10° and higher temperatures, say about 40° or 50° and more preferably up to about 60° or 65°.

In many embodiments of this invention polymeric materials that exhibit glass/rubber transitional behavior under tensile stress will exhibit yield at a stress between about 500 and about 9,000 psi. In preferred embodiments of this invention the polymeric materials will exhibit yield stress between about 1,000 and about 5,000 psi. In even more preferred embodiments, the polymeric materials will exhibit yield stress between about 2,000 and 4,000 psi. That is, with reference to FIG. 2 the polymeric materials will exhibit a stress strain deformation curve that at least passes beyond point "A" at the desired temperatures and in the desired range of yield stress.

In many preferred embodiments of the invention the polymeric material in ribbon form will exhibit a load/deformation curve that extends to at least point B of the curve of FIG. 2 indicating strain softening, i.e. necking, of the polymeric material under stress. In many other preferred embodiments, the polymeric material in ribbon form will further exhibit elongation after yield as indicated by region B-C of the curve of FIG. 2. Such elongation may vary depending, e.g. on the strain rate. In some cases the polymeric material can be fabricated into ribbon useful as a twist tie when the amount of deformation in elongation is small, e.g. less than about 30% or even smaller, say less than about 10% or even negligible. Such deformation in elongation is often followed by strain-hardening before failure. In preferred embodiments polymeric material fabricated into ribbons useful as twist ties will exhibit substantial deformation in elongation, e.g. at least about 50% or higher, say about 200% or more. Such deformation can be approximated by total deformation, since the total deformation through yield is often small compared to total deformation through elongation. In many preferred embodiments the load/deformation curve exhibited by polymeric material in ribbon form in the elongation region B-C will be substantially horizontal or slightly upwardly-sloped.

In order for ribbons to be useful as twist ties, it is desirable that the ribbon be capable of being twisted into a fastly held tie, untwisted and retwisted several times over, at least about 10 times, and preferably at least about 30 times or more. The requirement for such retwisting is based on the generally expected manual retying of ribbon to secure packaged materials, e.g. bread wrappers. Ribbons comprising polymeric materials that do not meet this criteria often exhibit fracture failure resulting from fatigue.

Such fatigue failure can be characterized by a "RETIE" parameter which is determined by manually twisting the ribbon with three full turns in one direction, untying the ribbon and retying with three full turns in the opposite direction and so forth until failure occurs. Ribbons of this invention should be capable of being multiply twisted in such alternating directions, e.g. exhibit a RETIE of at least 10 or more without failure. In preferred embodiments, ribbons will exhibit a RETIE of at least 30 without failure.

Another method of characterizing fatigue failure is by "DEADFOLD" which is determined by manually folding the ribbon in a 180° bend in alternating directions until fracture failure is observed. Polymeric material useful in the ribbons of this invention should exhibit at least 10 full 180° alternating bends before failure, i.e. exhibit a DEADFOLD of at least 10. Preferred materials will exhibit a DEADFOLD of at least 30 or more. In many preferred embodiments the ribbon of this invention will comprise a polymeric material that will allow the ribbon to exhibit a DEADFOLD of at least 50 or more without fracture failure.

Materials which have been found useful in preparing the ribbons of this invention will comprise any essentially organic polymeric material that meets the above-described physical criteria when in the form of a ribbon. For instance, such essentially organic polymeric materials in a ribbon form will at least (1) exhibit a glass transition temperature greater than about 30°, (2) exhibit glass/rubber transitional behavior in a temperature range from about 10° to about 40° and (c) will under tensile stress at 25° exhibit yield at a stress between about 500 and 9,000 psi. Preferred essentially organic polymeric material will, in a ribbon form, exhibit the more preferred characteristics described above.

Such essentially organic polymeric materials can include blends, alloys, and mixtures of compatible and non-compatible polymeric materials. It has been found that some organic polymers per se can meet this criteria; other organic polymers require the addition of an impact modifier; and still others will meet this criteria if blended with a plasticizer. With knowledge of the above-described criteria and the exemplary compositions described herein, such materials can be readily formulated by those skilled in the art. Useful polymers include polyalkylene terephthalates such as polyethylene terephthalates and polybutylene terephthalates, styrene-acrylonitrile copolymer, polyvinylchloride and polystyrene and mixtures thereof. In many preferred embodiments such polymers are present in amounts of at least about 50% of the polymer and even up to 100%, e.g. at least in the case of certain grades of polyethylene terephthalate and polyvinylchloride.

In many other preferred embodiments it is desirable to provide what is generally known as particulate rubber impact modifier at levels up to about 50%, for instance 5, 10, 20 or 30% of such impact modifier. Such impact modifiers can comprise elastomeric materials such as butadiene copolymer, blends of butadiene-styrene copolymer, butadiene-acrylonitrile copolymer and acrylic elastomers such as butylacrylate copolymers and mixtures thereof. A useful butadiene-acrylonitrile elastomeric material comprises a rubber graft copolymer having a rubber core of butadiene-acrylonitrile elastomer bonded to an occluding polymeric surface of styrene-acrylonitrile, such as disclosed in U.S. Pat. No. 4,510,287, Part A of Example 1. A useful acrylic elastomeric material comprises a multi-phase composite interpolymer having a rubber core of butylacrylate elastomer bonded to an occluding thermoplastic polymeric surface of methylmethacrylate, such as Acryloid KM-330 available from Rohm and Haas Company. Such impact modifiers have often generally been used in polymeric compositions at levels of up to about 10%. It has been surprisingly found that the use of impact modifiers in levels up to about 30% or more, e.g. even up to about 40% or even higher, provide exceptionally desirable properties to the polymeric materials useful in the ribbons of this invention.

To provide uniform properties for ribbons to be useful as twist ties it has been found that such impact modifiers are desirably provided in small particle size to afford uniform distribution of the impact modifier in the generally small cross-sectional shapes of the ribbons of this invention. Impact modifiers having particle size diameters less than about one millimeter, and preferably as low as about 2.5 millimeters or smaller, have been found to be advantageous.

In some instances it has been found that the mere addition of plasticizer to certain thermoplastic materials, e.g. polyvinylchloride, can provide a polymer as useful in the ribbon of this invention. Polymeric materials used in the ribbons of this invention can also comprise blends of thermoplastic materials, e.g. thermoplastic polymers and impact modifiers, and compatible plasticizers provided that the glass transition temperature of the thermoplastic material is not reduced to below an effective level, e.g. about 30° C. or higher, preferably not lower than about 50° or 60° C. Polymeric materials will also often advantageously contain other additives such as anti-oxidants, processing agents, e.g. metal organic salts, such as magnesium stearates, fillers such as calcium carbonate, pigments and the like.

Ribbons of this invention are advantageously provided in filamentary segments having a length which is very large as compared to its cross-sectional area, which is preferably substantially uniform prior to use as a twist tie. It is understood that the cross-sectional area will preferably deform when ribbon is twisted into a tie. The ribbon can be in any desired cross-sectional shape, i.e. substantially circular, oval, square, rectangular, star-shaped, lobed, flat and the like. In preferred embodiments, the ribbon will be substantially thin and flat; and in other preferred embodiments, the thin flat ribbon will have one or more ribs along its length.

Figure 4:
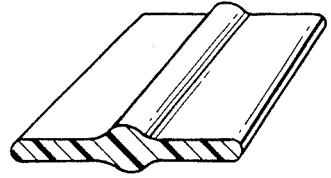
FIG. 4 illustrates a partial cross-sectional view of one embodiment of the ribbon of this invention.

An especially preferred embodiment is illustrated in FIG. 4, where the thin, flat ribbon has a central rib extending from both sides. Such ribbon can have a width from about 1 mm to about 10 mm or more, preferably from about 2 mm to about 6 mm. The central rib can be rounded, square or pointed and have an overall thickness from about 0.5 mm to about 4 mm or more, preferably from about 1 to about 3 mm.

This invention also provides a process for producing such ribbons. Polymeric materials are advantageously fabricated into ribbons according to this invention by extruding a mixed, molten polymer melt of the above-described polymeric materials through a die. In some cases double extrusion is preferred to achieve a more homogeneous melt. The ribbon is preferably extruded under tension and quenched by passing the ribbon through a water bath, e.g. at a temperature at least about 10° below the glass transition temperature of the polymeric material. The quenched ribbon is preferably taken up under tension, e.g. onto spools for storage before use as a twist tie. Ribbons according to this invention can also be provided in a perforated sheet form, where a sheet is extruded under similar conditions as used to produce ribbon. Such sheet is desirably perforated to allow discrete lengths of ribbon to be readily separated therefrom.

As previously noted, ribbon capable of being formed into twist ties have numerous uses. A particularly advantageous use is to close and secure bags, e.g. plastic bags containing food products such as bread or microwave-heatable food products. Methods of this invention for closing and securing bags comprise gathering an open end of the bag to form a constructed neck which can be encircled with a ribbon according to this invention. The ends of the ribbon are then twisted into a fastly held tie.

The following disclosure is provided to illustrate specific embodiments and aspects of this invention but does not imply any limitation of the scope of the invention.

EXAMPLE 1

This example illustrates the preparation of a ribbon of this invention comprising polyethylene terephthalate.

Polyethylene terephthalate, designated as KODAPET ® PET 7352, Eastman Kodak Company, ("PET") was dried in an oven at 130° for 12 hours, then melted and extruded through a die into a strand that was quenched in a water bath at about 20°. The quenched strand was chopped into pellets which were dried in an oven at 90° for 3 hours. The dried pellets were melted and extruded through a die into a ribbon that was quenched in a water bath at about 20°. Ribbon having a geometry similar to that illustrated in FIG. 4 was taken up under tension on a spool. The ribbon had a width of about 3.8 mm and a central rib extending from both sides of the ribbon to an overall thickness of about 1.2 mm. The ribbon had a basis weight of about 1.9 g/m.

In tensile analysis conducted at 20°, 50% relative humidity, the ribbon exhibited a load/deformation curve similar to that of FIG. 2 with deformation to a point in the B-C region indicating elongation after yield. The polymeric material of the ribbon was indicated to be in a glass/rubber transitional state at strain rates between 0.1 and 10.0 ipipm. The tensile analysis results are indicated in the following Table 1.

TABLE 1

| | Tensile Analysis | |
|---|---|---|
| Strain Rate, ipipm | Yield Stress, psi (MPa) | Deformation, % |
| 0.1 | 3650 (25.1) | >250 |
| 0.5 | 3950 (27.2) | >250 |
| 10.0 | 4420 (30.5) | 750 |

The ribbon, analyzed for fatigued failure, exhibited RETIE greater than 30 and DEADFOLD greater than 50 without failure.

The ribbon was utilized in an automatic bag closing and tying machine (model 50-7, Burford Corporation) at packaging rate of 60 bags per minute. The machine produced tight ties ("Machine Ties") having between 1 and 1½ twists.

Twist ties made from the ribbon were placed in an oven at 65° for 30 minutes; the ties did not untwist ("65° oven": twist held).

EXAMPLE 2-6

Examples 2-6 illustrate the preparation of ribbons according to this invention comprising PET and elastomeric impact modifiers.

PET dried as in Example 1 was mixed with polymeric materials selected from the following group:

(A) Acrylic elastomeric impact modifier, ACRYLOID® KM-330, Rohm and Haas Company which was dried in an oven at 80°-90° for 12 hours ("AIM");

(B) Butadiene-styrene thermoplastic elastomer, FINAPRENE 416 (70% butadiene/30% styrene block copolymer), FINA Oil and Chemical Company which was dried in an oven at 80°-90° for 12 hours ("BIM"); and (C) N-tallow, toluenesulfonamide plasticizer, MXP-2097, Monsanto Company, ("MXP").

As in Example 1 the polymeric mixtures were extruded to provide quenched strands which were chopped into pellets; the dried pellets were extruded into ribbons which were quenched and taken up under tension onto spools. Compositions and tensile analysis results of the ribbons are indicated in the following Table 2.

TABLE 2

| Example | Formulation, wt. % | Yield Stress,[a] MPa (psi) | Deformation,[a] % |
|---|---|---|---|
| 2. | 95% PET | 26.5 (3850) | >250 |
|    | 5% AIM  | 30.3 (4400) | >250 |
|    |         | 32.5 (4720) | 700 |
| 3. | 70% PET | 16.7 (2425) | >250 |
|    | 30% AIM | 20.0 (2900) | >250 |
|    |         | 26.9 (3900) | 600 |
| 4. | 61% PET | 14.0 (2025) | >250 |
|    | 30% AIM | 15.8 (2300) | >250 |
|    | 9% MXP  | 18.4 (2667) | 600 |
| 5. | 68% PET | 15.3 (2225) | >250 |
|    | 30% AIM | 16.9 (2450) | >250 |
|    | 2% MXP  | 18.9 (2750) | 400 |
| 6. | 70% PET | 12.9 (1875) | >50 |
|    | 30% BIM | 14.5 (2100) | >250 |
|    |         | 16.3 (2362) | 90 |

[a]Yield stress and deformation values are at strain rates of 0.1, 0.5 and 10.0 ipipm.

Each of the ribbons of Examples 2-6 exhibited RETIE greater than 30 and DEADFOLD greater than 50. All of the ribbons, except those of Examples 4 and 5, held tight twist ties while in an oven at 65° for 30 minutes. Machine ties of the ribbon of Example 2 had ½-1½ twists; of Examples 3-5, 1½ twists; and Examples 6 and 7, 1-1½ twists.

EXAMPLES 7-13

Examples 7-13 illustrate the preparation of ribbons comprising polyvinylchloride. Ribbons were prepared from among the following group of polymeric materials.

(A) AIM (as in Examples 2-6)
(D) Polyvinylchloride, GEON 30, intrinsic viscosity: 1.03, BF Goodrich Company, ("PVC 30");
(E) Polyvinylchloride, GEON 110, intrinsic viscosity: 0.68, BF Goodrich Company, ("PVC 110"); and
(F) Butyl benzyl phthalate plasticizer, S-160, Monsanto Company, ("S-160").

The polyvinylchloride material was dried in an oven at 130° for 12 hours. Polyvinylchloride and mixtures of polyvinylchloride and other polymeric materials were fed to an extruder, melted and extruded into a water bath at 20° to form a ribbon having a geometry similar to that illustrated in FIG. 4 which was taken up under tension on a spool. Compositions and tensile analysis results of the ribbons are indicated in the following Table 3.

TABLE 3

| Example | Composition, wt. % | Yield Stress[a] MPa (psi) | Deformation[a] % |
|---|---|---|---|
| 7. | 100% PVC 110 | 26.5 (3850) | >50 |
|    |              | 29.3 (4250)[b] | — |
|    |              | 35.2 (5100)[b] | — |
| 8. | 70% PVC 110  | 18.6 (2700) | >250 |
|    | 30% AIM      | 16.9 (2450) | >250 |
|    |              | 20.3 (2950) | 300 |
| 9. | 95% PVC 30   | 18.8 (2725) | 20 |
|    | 5% AIM       | 18.8 (2725) | 15 |
|    |              | 25.0 (3625)[b] | — |
| 10.| 90% PVC 30   | 33.1 (4800)[b] | — |
|    | 10% S-160    | 36.9 (5350)[b] | — |
|    |              | 42.0 (6100)[b] | — |
| 11.| 80% PVC 30   | 14.3 (2075) | >50 |
|    | 20% S-160    | 18.6 (2700) | 195 |
|    |              | 27.0 (3925)[b] | — |
| 12.| 60% PVC 30   | [c] | |
|    | 40% S-160    |     | |
| 13.| 75% PVC 30   | 21.9 (3175) | >50 |
|    | 15% AIM      | 21.7 (3150) | 185 |
|    | 10% S-160    | 27.9 (4050)[b] | — |

[a]Yield stress and deformation values are at strain rates of 0.1, 0.5 and 10.0 ipipm.
[b]Tensile stress at brittle failure before yield.
[c]Ribbon exhibited rubber-like behavior as illustrated in FIG. 3.

The ribbons were evaluated for fatigue failure and to determine if they would hold a twist tie at 65°; the results are indicated in Table 4.

TABLE 4

| Example | Fatique Analysis Retie | Fatique Analysis Deadfold | 65° Oven |
|---|---|---|---|
| 7. | 17 | 15 | held twist |
| 8. | 24 | >50 | held twist |
| 9. | 2 | 32 | held twist |
| 10. | 1 | 25 | untwisted |
| 11. | 10 | >50 | untwisted |
| 12. | [a] | [a] | [b] |
| 13. | 3 | 43 | untwisted |

[a]Ribbon was too resilient to fail by fatigue.
[b]Ribbon untwisted at 25°.

The results of machine tie analysis are reported in Table 5.

TABLE 5

| Example | Machine Tie, Twists |
|---|---|
| 7. | <1 |
| 8. | 1-½ |
| 9. | <1 |
| 10. | ½-1 |
| 11. | <1 |
| 12. | 0 |
| 13. | 1-1½ |

The above fatigue analysis results indicated that the ribbon of Examples 9, 10 and 13 are unacceptable for use as twist ties. The highly plasticized ribbon of Example 12 having a glass transition temperature less than 30° is also unacceptable for use as a twist tie.

EXAMPLES 14-15

Examples 14-15 illustrate the preparation of ribbon comprising polystyrene, Lustrex ® 4300, a high impact polystyrene, Monsanto Company ("HIPS") and comprising HIPS and AIM.

The HIPS was dried in an oven at 130° for 12 hours. The polymeric material was processed into pellets and then into ribbon as in Example 2. Compositions and tensile analysis results are indicated in the following Table 6.

TABLE 6

| Example | Composition, wt. % | Yield Stress[a] MPa (psi) | Deformation[a] % |
|---|---|---|---|
| 14. | 100% HIPS | 16.5 (2400) | >50 |
|  |  | 19.5 (2825) | 55 |
|  |  | 22.9 (3325) | 100 |
| 15. | 70% HIPS | 15.2 (2200) | >50 |
|  | 30% AIM | 15.8 (2300) | 80 |
|  |  | 18.5 (2675) | 150 |

[a]Yield stress and deformation values are at strain rates of 0.1, 0.5 and 10.0 ipipm.

The ribbons were evaluated for fatigue failure and to determine if they would hold a twist tie at 65°; the results are indicated in Table 7.

TABLE 7

| | Fatigue Analysis | | |
|---|---|---|---|
| Example | Retie | Deadfold | 65° Oven |
| 14. | 0 | 2 | — |
| 15. | 18 | 3 | held twist |

Although the ribbon of Example 14 exhibited yield and glass/rubber transitional behavior, fatigue analysis indicated that the ribbon was too brittle to be acceptable for use as a twist tie. The ribbon of Example 15 performed as an acceptable twist tie in machine tie analysis with 1½ twists.

EXAMPLE 16

This example illustrates the preparation of a ribbon comprising a polyblend of a butadiene rubber with a styrene-acrylonitrile copolymer.

A small particle size (e.g. about 0.18 microns) rubber graft copolymer comprising butadiene, acrylonitrile and styrene was prepared in accordance with Part A of Example 1 of U.S. Pat. No. 4,510,287 ("ABS"). The ABS was dried in an oven at 130° for 12 hours and mixed with AIM (prepared as in Example 2 above).

The polymeric mixture (90% ABS, 10% AIM) was melted and extruded into a water bath at 20° to form a strand which was chopped into pellets. The pellets were dried in an oven at 90° for 3 hours, melted and extruded into a water bath at 20° to form a ribbon which was taken up on a spool. The ribbon had a geometry similar to that illustrated in FIG. 4.

Tensile analysis results of the ribbon are indicated in Table 8.

TABLE 8

| Example | Yield Stress[a] MPa (psi) | Deformation[a] % |
|---|---|---|
| 16. | 15.7 (2275) | >50 |
|  | 17.2 (2500) | 75 |
|  | 19.4 (2817)[b] | — |

[a]Yield stress and deformation values are at strain rates of 0.1, 0.5 and 10.0 ipipm.
[b]Brittle failure at 10.0 ipipm.

Fatigue analysis indicated that the ribbon exhibited RETIE of 26 and DEADFOLD greater than 50.

In machine tie the ribbon formed a tight twist tie with 1½ twists. The twist ties held fast in an oven at 65° C. (3 hours).

While the invention has been described herein with regard to certain specific embodiments, it is not so limited. It is to be understood that variations and modifications thereof may be made by those skilled in the art without departing from the spirit and scope of the invention.

What is claimed is:

1. A wireless twist tie adapted to be twisted from a ribbon into a fastly holding closure comprising polymeric material exhibiting a glass transition temperature greater than about 30° C. and exhibiting glass/rubber transitional behavior in a temperature range from about 10° C. to about 40° C., wherein, when said twist tie is deformed under tensile stress at 25° C. at a strain rate between 0.1 and 0.5 inches per inch per minute, said twist tie exhibits yield at a stress between about 500 and 9,000 psi, said material comprising polyethylene terephthalate and particulate rubber impact modifier.

2. A twist tie according to claim 1 wherein said impact modifier comprises a rubber core and a thermoplastic polymeric surface.

3. A twist tie according to claim 2 wherein said core comprises butyl acrylate rubber and said surface comprises methyl methacrylate thermoplastic polymer.

4. A twist tie according to claim 1 which is adapted to be twisted into a fastly holding closure at a temperature of at least about 65° C.

5. A twist tie according to claim 1 which is adapted to be folded in full 180° bends at least about 10 times in alternating directions without failure.

6. A twist tie according to claim 1 which is adapted to be multiply twisted into a fastly holding closure at least about 10 times in alternating directions without failure.

7. A twist tie according to claim 6 which exhibits strain softening when deformed under tensile stress at a strain rate between 0.1 and 0.5 inches per inch per minute.

8. A twist tie according to claim 7 which exhibits elongation after yield and a total deformation before failure of at least 30% when deformed under tensile stress at said strain rate.

9. A twist tie according to claim 8 wherein said total deformation is at least 50%.

10. A twist tie according to claim 6 having a substantially uniform cross-section over its length in the form of a ribbon with a central rib.

11. A plurality of twist ties according to claim 6 joined in a continuous length.

12. A plurality of twist ties according to claim 6, separably joined in a sheet.

13. A wireless twist tie adapted to be twisted from a ribbon into a fastly holding closure comprising polymeric material having a glass transition temperature greater than about 30° C. and exhibiting glass/rubber transitional behavior in a temperature range from about 10° C. to about 40° C., wherein, when said twist tie is deformed under tensile stress at 25° C. at a strain rate between 0.1 and 0.5 inches per inch per minutes, said twist tie exhibits yield at a stress between about 500 and 9,000 psi, said polymeric material comprising polyethylene terephthalate.

14. A twist tie according to claim 13 comprising polyethylene terephthalate and styreneacrylonitrile copolymer.

15. A wireless twist tie according to claim 13 adapted to form fastly holding ties when used in an automatic bag closing and tying machine.

16. A twist tie according to claim 15 comprising particulate rubber impact modifier.

17. A twist tie according to claim 16 adapted to be a fastly holding closure at temperatures of at least 65° C.

18. A twist tie according to claim 15 wherein said machine is a Burford Corporation Model 50-7.

* * * * *